United States Patent [19]

Davis

[11] 4,408,600
[45] Oct. 11, 1983

[54] LEG AID DEVICE AND METHOD

[76] Inventor: Edward P. Davis, 1446 Delaware Ave., West St. Paul, Minn. 55118

[21] Appl. No.: 344,363

[22] Filed: Feb. 1, 1982

Related U.S. Application Data

[63] Continuation-in-part of Ser. No. 146,142, May 2, 1980, abandoned.

[51] Int. Cl.³ .................. A61F 3/00; A41D 13/00
[52] U.S. Cl. ............................. 128/80 R; 2/22
[58] Field of Search ............... 128/80 R, 80 C, 80 F, 128/89; 2/22; 36/2.5 AC

[56] References Cited

U.S. PATENT DOCUMENTS

| | | | |
|---|---|---|---|
| 604,044 | 5/1898 | Hamel et al. | 128/80 |
| 1,354,427 | 9/1920 | Welter | 128/80 |
| 1,510,408 | 9/1924 | Lychou | 128/80 C |
| 2,567,195 | 9/1951 | Ellery | 128/80 |
| 2,571,717 | 10/1951 | Howald et al. | 43/18 |
| 2,573,698 | 11/1951 | Ellery | 128/80 |
| 2,712,310 | 7/1955 | Giambra | 128/80 |
| 2,772,674 | 12/1956 | Swiech et al. | 128/80 |
| 2,871,852 | 2/1959 | Miller | 128/80 |
| 2,934,064 | 4/1960 | Invidiato | 128/80 |
| 2,949,111 | 8/1960 | Ruotoistenmaki | 128/80 |
| 3,026,869 | 3/1962 | Peach | 128/80 |
| 3,084,685 | 4/1963 | Lewis | 128/80 C |
| 3,528,412 | 9/1970 | McDavid | 128/80 |
| 3,589,359 | 6/1971 | Hill | 128/80 |
| 3,799,159 | 3/1974 | Scott | 128/80 C |
| 3,826,251 | 7/1974 | Ross | 128/80 F |
| 3,900,898 | 8/1975 | Ackerman | 2/22 |
| 3,928,872 | 12/1975 | Johnson | 128/80 C X |
| 3,993,056 | 11/1976 | Rabischong et al. | 128/89 R |
| 4,050,455 | 9/1977 | Smith | 128/80 F |
| 4,100,918 | 7/1978 | Glancy | 128/80 F |
| 4,115,902 | 9/1978 | Taylor | 16/179 |
| 4,130,115 | 12/1978 | Taylor | 128/80 C |
| 4,136,404 | 1/1979 | Lange | 2/22 |

FOREIGN PATENT DOCUMENTS

| | | |
|---|---|---|
| 838479 | 5/1952 | Fed. Rep. of Germany . |
| 2238038 | 2/1973 | Fed. Rep. of Germany . |
| 121322 | 12/1918 | United Kingdom . |

*Primary Examiner*—Stephen C. Pellegrino
*Attorney, Agent, or Firm*—Robert C. Baker

[57] ABSTRACT

A leg aid device and method for increasing the stamina of a body-supporting user's leg for repeated flexure and extension at the knee. The device comprises elongated flexibly resilient biasing means for placement in approximate alignment with a user's leg from a level near the ankle area up to at least the level of the mid-thigh area. The biasing means is adapted to bias a user's leg toward a straightened condition without significant torsion or twisting of the leg. Holding means maintains the biasing means approximately aligned upon a user's leg for bending yieldingly therewith into an overall arcuate form during flexure of the leg at the knee. The biasing means, when held by the holding means upon a body-supporting user's leg, functions to support a portion of the user's body weight during times the biasing means is in bent condition with the user's leg in flexed condition, and functions to aid the user's leg muscles in causing extension of the user's leg from flexed condition as the biasing means resiliently returns toward a straightened condition with the extension of the user's leg.

28 Claims, 25 Drawing Figures

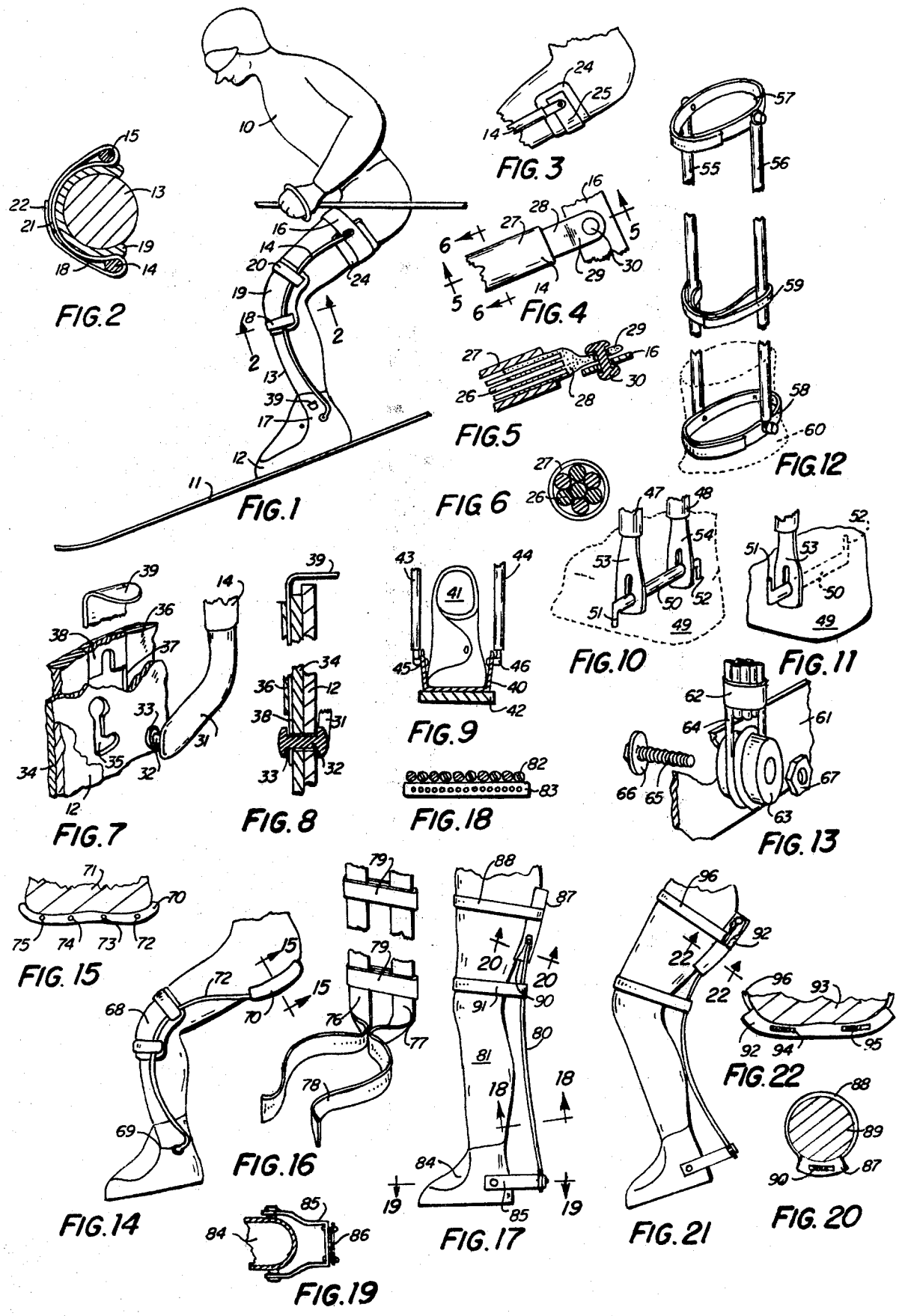

LEG AID DEVICE AND METHOD

CROSS REFERENCE TO RELATED APPLICATION

This application is a continuation-in-part of my application Ser. No. 06/146,142, filed May 2, 1980 now abandoned.

FIELD OF THE INVENTION

This invention relates to a leg aid device and a method for increasing the stamina of a leg repeatedly flexed and extended at the knee, and more particularly, to a leg aid device having biasing means as an essential part thereof.

The biasing means aids in supporting a portion of a user's body weight when the user's leg is flexed (i.e., bent) at the knee. When the user extends his leg (i.e., straightens it), the biasing means springs back toward a straightened condition, and thereby aids the user's leg muscles in causing extension of the leg and resulting upward movement of the user's body. In effect, the leg muscles of the user are relieved from some, but not all, of the strain they undergo during flexure and extension.

The device contributes greatly to increased enjoyment of skiing. The main usefulness of the device is to increase leg stamina without interfering with leg functions, without any significant leg torsion or twisting, as desired by skiers and others engaged in athletic or sport activity involving repeated flexure and extension of the leg.

DESCRIPTION OF THE PRIOR ART

Leg devices having elongated means for placement upon a user's leg and holding means for maintaining the elongated means on the leg are known. A leg aid device hinged for knee movement is known for skiers, as is one employing torsion bars as spring members. Neither functions in the manner of the device taught herein. Torsion bars as spring beams are so stiff as to be incapable of being mounted on a skier to give performance for the functions taught herein. A variety of orthopedic appliances are old. Some cause torsion or twisting of a user's leg; others are mere guide devices. No prior art leg appliance is known to have the properties and perform the functions of the devices taught herein.

SUMMARY OF THE INVENTION

The leg aid device comprises elongated means for placement upon a user's leg and holding means for maintaining the elongated means upon the user's leg.

The elongated means consists essentially of elongated flexibly resilient biasing means having a length sufficient for placement in approximate alignment with the user's leg from a level near the ankle area up to least the level of the mid-thigh area and having a flexibility sufficient for the length to be repeatedly yieldingly bent into at least a semi-circle without taking on a permanent set. The biasing means, when held upon a body-supporting user's leg by the holding means hereinafter recited, functions to support a portion of the user's body weight during times the user's leg is in flexed condition and functions to aid the user's leg muscles in causing extension of the user's leg from a flexed condition.

The holding means consists essentially of (i) a lower holder for fastening the lower end of the biasing means at a level near the user's ankle area, (ii) an upper holder for fastening the upper end of the biasing means at a level at least as high as the user's mid-thigh area, and (iii) an intermediate holder comprising means for applying a forward pulling force transversely upon the biasing means at a mid-portion thereof at the level of the user's knee area. The intermediate holder is separate from the lower and upper holders but functions in cooperation therewith to cause the biasing means to urge the user's leg toward a straightened condition without significant torsion or twisting of the user's leg and also functions in cooperation therewith during leg flexure to cause the biasing means to take on an arcuate contour throughout substantially the entire length of the biasing means.

The biasing means of the main embodiment comprises two elongated flexibly resilient biasing members which in use extend at their mid-portion on opposite sides of a user's knee area and are mounted for movement along or so as to be maintained along opposite lateral portions of a user's leg. In an alternative embodiment, having special advantages onto itself, especially for skiers riding chair lifts, the biasing means comprises a biasing member for placement behind the leg. In all embodiments, the biasing members preferably comprise a bundle or grouping of a plurality of elongated flexible elements.

The invention additionally includes the method of increasing the stamina of a leg for repeated flexure and extension at the knee in physical activity involving leg support of the body. This method comprises forming and fastening elongated flexibly resilient biasing means in substantial alignment with a leg from a level near the ankle area up to at least the level of the mid-thigh area, and applying a forward pulling force at the mid-portion thereof. Repeatedly flexing and extending the leg at the knee causes a portion of the weight of the body to be supported by the biasing means during times the leg is in flexed condition, and further causes the muscles of the leg to be aided by the biasing means as the biasing means resiliently returns toward a straightened condition when the muscles extend the leg from a flexed condition.

Additional features and relationships and advantages of the invention are described below, with the aid of a drawing, made a part hereof.

THE DRAWING

Schematic illustrations are employed; and in all Figures, parts are broken away.

FIGS. 1 through 15 deal with preferred embodiments which employ laterally disposed biasing members:

FIG. 1 is a side plan view of a skier equipped with the device;

FIG. 2 is a sectional view taken on line 2—2 of FIG. 1;

FIG. 3 is a side plan view of a "saddle" upper holder for the thigh area;

FIG. 4 is an enlarged side plan view of a fastening structure between a biasing member and the upper holder;

FIG. 5 is a sectional view taken on line 5—5 of FIG. 4;

FIG. 6 is a sectional view taken on line 6—6 of FIG. 4;

FIG. 7 is a fragmentary exploded perspective view of the lower holder at the footwear portion of the device in FIG. 1;

FIG. 8 is a vertical sectional view through the lower holder fastening elements shown in FIG. 7;

FIG. 9 is a front view, partially in section, illustrating a stirrup or under foot arrangement for a lower holder;

FIGS. 10 and 11 are perspective fragmentary views of the heel area of a boot, shown as a phantom fragment, and illustrate two different settings for an alternative under foot lower holder;

FIG. 12 is a perspective view of a simplified device, with a boot shown as a phantom fragment;

FIG. 13 is an exploded perspective view of an alternative fastening means between biasing means and a holding means at either the upper or lower end of the biasing means; and FIGS. 14 and 15 deal with a further variation, with FIG. 14 a side plan view and FIG. 15 a sectional view taken in line 15—15 of FIG. 14.

FIGS. 16 through 22 deal with embodiments employing biasing means mounted behind a user's leg:

FIG. 16 is a perspective view, with the upper parts broken away but analogous to those illustrated in FIG. 17;

FIG. 17 is a side plan view of a strip biasing means;

FIG. 18 is a sectional view, taken on line 18—18 of FIG. 17, illustrating two different types of strip biasing members;

FIG. 19 is a partial sectional view, taken at line 19—19 of FIG. 17, and illustrates a lower holder;

FIG. 20 is a sectional view, taken at line 20—20 of FIG. 17, and illustrates the upper holder and slot arrangement for slidable mounting of the upper end of the strip biasing means;

FIG. 21 is a side plan view with the user's knee partially bent; and

FIG. 22 is a sectional view, taken on line 22—22 of FIG. 21, and illustrates a possible seat arrangement for an upper holder which has two slot recesses for slidably receiving strip biasing means of each leg.

Figure 23:
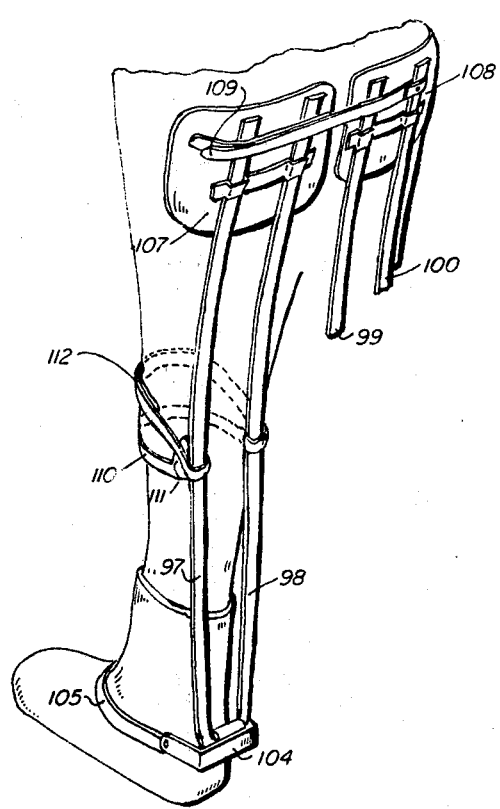
Figure 24:
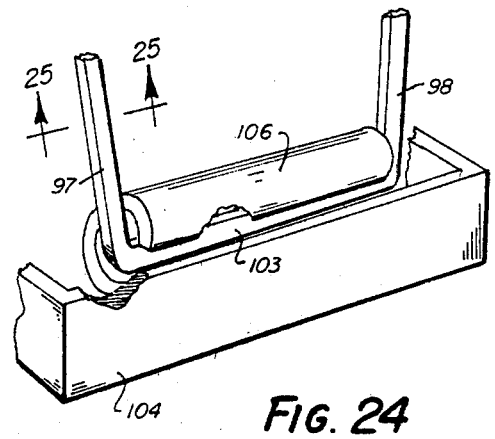
Figure 25:
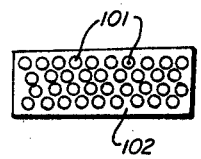

FIGS. 23 through 25 deal with the most preferred specific embodiment of the invention;

FIG. 23 is a perspective view of the device on a skier, with parts broken away;

FIG. 24 is a perspective enlargement of the lower holder; and

FIG. 25 is a cross section taken on line 25—25 of FIG. 24

DESCRIPTION OF THE PREFERRED EMBODIMENTS

In FIG. 1, a skier 10 equipped with skis 11 and ski boots 12 is shown with his legs 13 in flexed condition. Therefore the biasing means 14, 15 on his legs is in a yieldingly bent condition. Only one side of one leg is viewable in FIG. 1; but the inside lateral part of that leg is equipped with the same elements (see FIG. 2) as shown on the outside viewable in FIG. 1.

Ordinarily both legs of a user will be equipped with biasing means according to the invention; but for descriptive purposes, the device of the invention will be detailed by making reference to a device for one leg only.

The biasing means comprises two biasing members 14, 15, each of which is elongated and normally substantially straight and always flexibly resilient. The resilience of the biasing members is that of returning from a bent condition to a relatively straight non-stressed condition. They are not mere stretchy elastic members. The two biasing members 14, 15 are along opposite lateral portions of a user's leg. They are in approximate alignment with the user's leg from a level near the ankle area up to at least the level of the mid-thigh area.

The holding means for maintaining the biasing means (members 14, 15) approximately aligned upon the user's leg for bending yieldingly therewith during flexure of the leg at the knee includes an upper holder 16, a lower holder 17, and an intermediate holder 18.

As illustrated in FIGS. 1 and 2, the intermediate holder has a knee pad 19 for fitting over the knee and extending on lateral sides of the knee far enough to serve as a pad to prevent chaffing of the biasing members 14, 15 against the lateral sides of the user's leg at the knee area. The pad may consist of any suitable material such as flexible foam or quilted material, with or without a stiffened outer knee cup. Strap means consisting of two strap members 18, 20 are illustrated and function to maintain the mid-portion between the ends of the biasing members 14, 15 at a location adjacent the knee area and at a location along opposite lateral portions of the knee area. The straps may be formed out of any suitable material, such as canvas, leather, plastic or the like. They may be integral with the knee pad or united to it or even possibly separate from it. In any event, at least one of the straps 18, 20, and preferably both, are connected to the biasing members on opposite lateral sides of the knee area. Illustratively, lower strap 18 extends over the lower edge of the knee pad 19 (and therefore over the front of the leg) and is wrapped around the laterally disposed biasing members 14, 15; and then the ends 21, 22 of the strap 18 are brought forward and united together by any suitable fastening means, whether a buckle or a "Velcro" fastener or a tie or otherwise. "Velcro" fasteners, and also those called "Scotchmate", are most useful. They all have a surface array of knobbed or hooked elements interlockable with a surface array of cooperatively mating character. The important feature to recognize is that the intermediate holder, regardless of its specific character, whether a simple strap or otherwise, does not necessarily extend around the entire leg of a user at or near the knee area. Such would be uncomfortable on bending of the knee; and the function of the intermediate holder is to maintain the mid-portion of the biasing members 14, 15 along opposite lateral portions of the knee area during bending of the knee. In effect, the intermediate holder therefore need only extend over the forepart of the leg of the user at or near the knee area, as illustrated.

The upper holder 16 maintains or fastens upper portions of the biasing members 14, 15 along opposite lateral portions of a user's thigh area. In FIG. 1, it is shown as a strap 16 wrapped around the mid-thigh portion of the leg, with ends of the strap fastened together. A pad 24 contributes to comfort.

As illustrated in FIG. 3, the upper holder may simply consist of a linking member or strap or contoured plate 25, suitably with pad 24, between the upper ends of the biasing members. It suitably embraces or extends only about the back or rear part of the user's thigh. The reason for this is because of the forces acting upon the biasing members in actual use. Since the biasing members 14, 15 are more or less fixed at the footwear or ankle level or area, all that is needed to hold them aligned upon the leg of a user is a means at the knee area for a forward pulling action, and a means at the uppermost ends for a rearward pulling action. The biasing members themselves oppose the pulling forces of these holders, and tend always to pull in the opposite direction, urging toward a straightened leg condition. Analytically, the forward pulling action or force of the intermediate holder is applied transversely upon the biasing members at a mid-portion thereof. This force pulls that mid-portion into a forwardly stressed condition at the user's knee level. The upper and lower holders effectively apply opposing forces at the ends of the biasing members. The result is that all three holders cooperate functionally to cause the biasing means always to urge the user's leg into a straight fully extended condition without significant torsion or twisting of the user's leg.

Now reference is made to FIGS. 4, 5, and 6, for a discussion of cooperative elements for connection between the upper end of the biasing members 14, 15 and the upper holder 16, as well as some preferred details of structure for the biasing members themselves.

The biasing members 14, 15 are not a single solid unitary metal rod. They suitably comprise a plurality of elongated substantially straight flexibly resilient biasing elements or wires 26, closely bunched together, and therefore considered to be a bundle, as particularly illustrated in FIGS. 5 and 6. Elements 26 may consist of black oil tempered spring wire having a diameter of about 2.66 millimeters (or about 0.105 inch). A group of, for example, 3 to 20 such elements (varying depending on the diameter and biasing strength) may be surrounded by a flexible sheath outer covering 27, such as a tube of polyethylene or other flexible plastic or rubbery material. Optionally, they need not be within a sheath; or they may be wrapped in their entirely at spaced locations with any suitable flexible tape. Biasing elements of this type are usually not embedded in any matrix of material for at least the major portion if not all (except their ends) of their length. They optionally may be embedded in a flexible plastic such as, for example, polyethylene or a flexible epoxy resin; but such introduces a dampening effect upon their resiliency, and is in most cases not desired. A non-embedded arrangement allows each wire to shift slightly with respect to its neighbors in the bundle, thereby exhibiting its highest resiliency even at higher bending, without significant dampening and with less tendency toward permanent set at higher bending.

As illustrated in FIG. 5, the ends of the elements 26 may be embedded and fixed within a solid mass 28 of metal or of tough sturdy organic plastics material such as, for example, one of phenolic or epoxy or nylon. This may be desirable for safety reasons, so as to obstruct shifting of the elements outwardly at the ends. A ferrule band or cap of metal may be employed at the ends, with or without embedding material. The material at the ends of the biasing elements suitably may be shaped so as to form an ear 29 extending longitudinally outward. A rivet 30 or other suitable fastener may be placed through a hole in the ear 29 and a hole in the upper strap holder 16 (or linking member 25). This allows some slight pivotal movement of the upper ends of the biasing members with respect to the upper holder. The slight pivot action occurs as the user flexes his legs from an extended condition. The illustrated biasing members assume a graceful curvature with respect to the leg, which is more angular; but even so, the biasing members are still maintained in approximate alignment with the user's flexed leg, as illustrated in FIG. 1.

The lower holder of FIG. 1 comprises fastening means at opposite lateral portions of the footwear of the user. One such fastening means, and the cooperative elements at the lower end of a biasing member for removably fastening the same, is illustrated in FIGS. 7 and 8. The lower end of the biasing member 14 terminates in a forwardly extending curvature of hook 31 suitably made of metal or any tough sturdy material, including plastics. (The biasing elements within the biasing member 14 are suitably unified at this lower end in a manner comparable to that discussed with respect to FIGS. 5 and 6.) Hook 31 is provided with an inwardly (toward user) projecting shaft 32 terminating in an expanded annular bulge or flange 33. Embedded in each lateral side of the boot 12 is a plate 34 having an "L" shaped opening 35 in it, with the upper portion of the "L" shape enlarged. The bulge terminus 33 is slipped into the "L" shape and slid along its legs to the lower end of the "L". Behind the plate 34 is a fixed rigid metal housing 36 having a groove 37. Key 38 is hand slidable in groove 37 by handle tab 39, and is slid down the groove 37 and locked over the bulged knob 33. This fastening means also permits a slight pivot movement between the fastening structure and the end of the biasing member 14.

The biasing members 14, 15 when separated from the skier are substantially straight; but mounting upon the leg of the skier will cause some slight curvature of them even when the skier's leg is in a fully extended condition. In effect, substantially straight biasing members are approximately aligned with the user's leg; and they bias the skier's leg toward a straightened condition without torsion or twisting of the legs. But the holding means (i.e., the upper 16 and lower 17 and intermediate 18 holders) maintain the biasing members approximately aligned upon the user's leg regardless of whether the leg is in flexed or extended condition.

In FIG. 9, the illustrated lower holder comprises a stirrup 40 attached to the sole of a boot 41 on a ski 42. The lower ends of the biasing members 43, 44 are fastened to the stirrup member by cooperative means such as a nut and bolt assembly 45, 46.

In FIGS. 10 and 11, the lower holder fastening means consists of a shaft 50 extending transversely through the heel structure and key elements 51, 52 projecting radially out from each end of the shaft. At the lower end of each of the biasing members 47, 48 is an ear 53, 54 having a circular hole and a key slot extending upwardly. The lower ends 53, 54 of the biasing elements are slid upon the shaft 50 with the key elements 51, 52 positioned upwardly as in FIG. 11. Then the key elements are turned downward to a locking position as illustrated in FIG. 10.

FIG. 12 shows two biasing members 55, 56, each comprising a bundle of a plurality of elongated flexibly resilient elements. The showing illustrates the most simple strap-type upper 57, lower 58, and intermediate 59 holders. The fastening means for the holders may be of the "Velcro" type aforementioned. The ends of the biasing members are fastened to the upper and lower holders in a manner allowing for some pivot movement of the ends. The lower strap holder is adapted to be wrapped around the ankle area of the boot 60 of a user. The intermediate strap 59 is placed over the forepart of the leg suitably at a location either just above or just below the knee. To keep strap 59 from shifting along biasing members 55 and 56, it may be fixedly fastened as by adhesive to them. When mounted on a user's leg, the biasing members 55, 56 remain in substantial approximate alignment during flexure and extension, even though they assume a curvature type bend, as distinguished from a sharp bend at any one particular point along the length of them.

In FIG. 13, a bundle 62 of resilient biasing elements is shown with at least one resilient element or wire 64 wrapped around a sleeve 63 in a spiral manner and then brought back into the bundle 62. The bundle is suitably taped or equipped with a ferrule ring. The fastening means for fixing the end of the resilient biasing member 62 to the strap holder 61 consists of a bolt 65, washer 66, and nut 67.

FIGS. 14 and 15 show a device (including holders 68 and 69) identical to that of FIG. 1 except for the upper holder. The upper holder comprises a seat member 70 contoured to the buttocks 71 of a user, with the upper ends of the biasing members 72, 73 and 74, 75 suitably fixed to the seat member. The seat member preferably is slightly curved about the buttocks lateral sides, and is padded for comfort. It is suitably molded out of relatively stiff plastics material, such as a fiberglass reinforced polyester resin. Further, it is most preferably formed in two parts, one for each buttocks, united together at the center line by a flexible but tough web or strap such as one of flexible tough fabric, or a rubberized or elasticized material. This permits greater comfort, since each part then may shift with its respective buttock in walking or flexing movements. The biasing members are spaced appropriately so that the pairs of biasing members extend on opposite lateral sides of each thigh of the user.

Reference is now made to FIGS. 16 through 22 of the drawing which illustrate biasing means behind the leg.

In FIG. 16, the biasing support is formed out of two solid bands or strips of spring steel or equivalent. Each band 76, 77 is contoured so as to form a clip member 78 to grip the ankle of a user from the rear. The bands extend up the rear of the user's leg; and in remaining respects, the device in FIG. 16 is comparable to that in FIG. 17. The two adjacent bands may be banded 79 together at intervals, as illustrated.

In FIGS. 17 through 20, the biasing means comprises a strip biasing member 80 for placement behind the leg 81 of a user. The member 80 may be a single solid band of resilient material, relatively flat in nature. Preferably, it is comprised of a plurality of elongated flexible elements substantially aligned. A flat array strip may solely consist of a single layer 82 (see FIG. 18) of elongated flexibly resilient substantially straight biasing elements. Also in FIG. 18 is a second flat array 83 of elongated flexible elements (e.g. glass fibers, spring metal wires) bonded and embedded within a flexible plastic, such as, for example, a flexible epoxy. Either such flat array or layer of elements may be employed singly as a strip biasing member; but two or three strip layers as a combination are also useful. The lower holder 84 comprises footwear equipped with a "U" shaped bracket 85. Any suitable clamp 86 or other means may be employed to secure the lower end of the strip biasing member 80 to the bracket 85. (This general arrangement is also useful as the lower holder for the laterally spaced biasing members illustrated in FIG. 1.) The upper holder comprises a receiving means 87 equipped with a belt or strap 88 for fastening it to the rear of the upper thigh 89. A slot recess 90 extends into the receiving means 87 and is adapted to receive the upper end of the strip biasing member 80 and allow slide movement (i.e., a longitudinal shift) of that strip biasing member therewithin. The intermediate holder may consist simply of a strap or belt 91 encompassing both the strip biasing member 80 and the leg 81 at a location proximate to the knee and preferably just above the knee. The intermediate holder strap 91 is tightened by the user sufficiently so as to effectively draw the biasing strip into a forwardly stressed condition at the user's knee area; and this is accomplished in a manner also causing the strip biasing member 80 to yieldingly bend on flexure of his knee without causing discomfort at the calf of his leg. Skiers equipped with the device illustrated in FIG. 17 find it especially comfortable to leave the device in operable mounted position on their legs while sitting in a chair lift. When a person equipped with this device of FIG. 17 desires to be relieved of the assistance afforded by the device for leg flexure and extension, but does not desire to completely remove the device from his leg, the intermediate strap holder 91 is unfastened or is loosened. In that condition, walking for the average person is made easier.

To be recognized is that as a skier bends a leg equipped with the device of FIG. 17, with the holder 91 drawn and fastened, the strip biasing member 80 bends and also slides upwardly in the slot 90 of the receiving member 87. Extension of the leg in turn causes the upper end of the strip biasing member 80 to slide downwardly in the receiving member.

The device illustrated in FIG. 21 is identical to that of FIG. 17, except for the upper holder illustrated in FIGS. 21 and 22. Receiving member 92 is especially contoured so as to fit the buttocks 93 of a user. Two slot recesses 94, 95 extend within the receiving member 92, one for the strip biasing member of each leg. A belt or strap 96 fastened to the receiving member 92 is wrapped about the user at his hip area.

FIGS. 23 through 25 illustrate the most preferred specific embodiment of the invention. Biasing members 97, 98 are in spaced condition for one leg; and another pair 99, 100 is for the other. The cross section of each member is suitably rectangular, as illustrated in FIG. 25. The members are oriented so that the least thickness undergoes the yieldable bending. Each member suitably consists of a plurality of elongated fibers or filaments 101, preferably of fiberglass or the like, bonded and bundled together by a suitably flexible resinous matrix or binder 102 such as, for example, a matrix of epoxy or polyester resin. The resinous matrix is preferably cured and the technology of making fiberglass reinforced resin structures is itself well known. Aligned fiberglass within the resinous matrix is employed, but for added strength or unification, some lengths of fiberglass may be placed on the bias.

As best illustrated in FIG. 24, the lower end of the pair of biasing members for a leg is united by a cross bar 103 suitably also formed of fiberglass reinforced resin and molded integrally with the end of the biasing members so as to form a unitary structure. The upper ends of the biasing members may be so united, if desired. Illustratively, the cross bar 103 is rectangular in cross section with the orientation of the narrowest width in the same plane as the narrowest width of the biasing members themselves, for reasons which will be hereinafter evident.

The placement of these biasing members on a leg is such that the upper and lower ends are located rearwardly of the leg. The biasing members themselves are spaced as to pass on flexure to the sies of the leg as they assume the curvature type bend or overall arcuate curvature characteristic of all biasing means of this invention.

The lower holder 104 suitably is mounted on the boot of a user, either as a permanent part or by means of a strap member 105. The structure of the lower holder 104 basically consists of a bracket or brace member having a horizontally extending structure 106 suitably in the nature of a sleeve with a horizontal slit opening facing rearwardly. The width of the slit opening is such that the narrower width of the lower cross bar 103 is easily slid through the slit, but the wider dimension of the lower cross bar is greater than the width of the slit. Thus, a user simply slips the lower cross bar of the assembly through the slit into the sleeve or recess while holding the biasing members in a horizontal plane, and then rotates the biasing members upwardly behind his leg. In doing so, the lower end is "locked" against displacement from the slit recess.

The upper holder illustratively simply consists, in each instance, of a buttocks or upper thigh plate 107, 108 to which the upper ends of the biasing members are suitably permanently fixed, either by molding the same thereto or by an adhesive or by any suitable clamp fasteners. Preferably, even when the upper holder is in the nature of a contoured seat member, the part of the holder for the biasing members of one leg is separable from the other. After the separate parts are in position, they are suitably united by a strap means 109 or the like extending from one part to the other and fastened as by "Velcro" fastening means.

The key attachment to the leg occurs when the mid-portion of the biasing members is drawn forwardly and placed under stress at the knee area. Illustratively, a single strap length 110 having a laterally projecting tab 111 is wrapped around one biasing member 97 and fastened as by "Velcro" to tab 111. Then the strap is placed over the leg below the knee, wrapped behind the other biasing member 98, brought forward above the knee, and drawn and fastened to the other end of the strap at 112. This is done in a manner which applies a forward pulling force transversely upon the biasing members at a mid-portion thereof to draw the mid-portion into a stressed condition at the level of the user's knee area.

In all embodiments of the invention, the biasing means is substantially straight when in non-stressed condition apart from the leg of a user. This is true even though some slight curvature may be built into the biasing means or members. For example, a pair of biasing members for a leg might be formed to exhibit, in non-stressed condition, a slight forward curvature, or a slight laterally outward curvature, between the ends thereof. However, the fundamental point is that the biasing members are not formed so as to be normally in a bent condition making them ineffective to bias a leg to a straight condition when mounted as aforedescribed on a leg. They are therefore properly characterized as substantially straight.

Discussion now will center on several concepts and principles which will further aid in understanding the invention.

The knee bending of a human's body-supporting leg, when equipped with a device as taught herein, causes the energy of downward body movement, which accompanies the knee bending, to be absorbed by the biasing means as it yieldingly also bends. So long as the knee remains in flexed or bent condition, the biasing means likewise remains in that condition, and functions to store the energy of the downward body movement. The body weight is partially supported by the bent biasing means, which in turn maintains the biasing means in that bent condition without extra effort by the leg muscles to keep it that way. Leg muscles of a flexed leg also exert some effort in supporting a portion of the body weight, albeit less than they would without the assistance of the bent biasing means. When the leg muscles are used to extend the leg, the stored forces of downward body weight in the biasing means are released; and they assist the leg muscles in accomplishing extension of the leg. In effect, when the leg muscles act to extend the leg, they take on the function of relieving some of the force of body weight on the biasing means. That relief of force results in movement of the biasing means toward a straightened condition because of its tendency to resiliently return to a straightened condition. As it resiliently returns to a straightened condition, the biasing means constantly exerts an upward pressure on the thigh or upper thigh or buttocks of a user, which in turn effectively causes the biasing means to assist the thigh muscles in executing leg extension, relieving them of some body weight support in doing so. Additionally, the biasing means assists in causing upward movement of the user's torso or main body weight. Thus under flexed conditions—whether toward a flexing, preserving or maintaining it, or movement out of flexing toward extension—the user's body-supporting leg muscles are relieved from some of their stress and strain in supporting the user's body weight, but not enough to interfere with normal leg muscle function. The relief, however, is sufficient to enhance the stamina of the leg muscles for repeated flexure and extension. This is extremely beneficial for devoted skiers. Many skiing accidents occur after leg exhaustion as a result of pushing oneself beyond normal endurance limits. By use of the device of this invention, there is much less likelihood of leg exhaustion and therefore accidental injury after several hours of skiing. As such, the device constitutes a new way to improve safety, and a new way to improve endurance, with full enjoyment of the sport.

Biasing members mounted on opposite lateral sides of a leg are balanced or substantially equal in their biasing tendency, thereby operating to maintain the leg substantially free from torque or twisting or from being pulled to one side or the other during leg flexure. The rear or back of leg position for biasing means also is effective for such result. In most cases, except where one leg is notably weaker than the other, it is preferable that each leg be biased to the same extent.

Different people using a device according to this invention may desire different degrees of weight relief and leg assistance, but operative and effective assistance to improve leg stamina is considered, as a result of testing, to be not less than a minimum total weight "lift" of approximately 3 kilograms or 7 pounds for a user whose legs are in a flexed condition of about 90° (i.e., the thigh and lower leg at about a 90° angle).

Stated another way, a minimum total "lift" of about 5% of a user's total body weight should be exhibited by effective biasing means on legs at 90°. As "lift" is increased beyond 70% or so of a user's total weight, even up to the highest "lift" of full body weight, there is introduced possible hazards or possible dangers arising from removing too much control from the leg muscles. Rarely will a "lift" in excess of 70 kilograms or about 150 pounds be desirable; and such high levels of total "lift" are useful mainly for those of relatively higher body weight. For many applications, a total "lift" in excess of about 5 kilograms or about 10 pounds, preferably at least 10 kilograms or 22 pounds, but not over about 45 kilograms or 100 pounds, will be found most useful and effective to increase leg stamina with an appropriately high safety factor. This preferred range is useful for persons weighing from about 40 kilograms or about 90 pounds up to about 90 kilograms or about 200 pounds.

The amount of "lift" exerted by an individual elongated biasing means (of length from ankle level to the mid-thigh level) is easily approximated by placing one end of it on a weight scale and pressing the other end against the scale until the length of the biasing means is yieldingly bent into approximately a semi-circle. The weight reading (less the weight of the biasing means per se) is considered to be an approximation of its "lift", for it approximately represents the force exerted by the bent biasing means against the force of bending it. The force of bending it, can be considered the approximate body weight "lifted" or supported by it for a 90° knee flexure by the user. It is emphasized that this is but an approximation; the exact location of the biasing member ends on a thigh affects the leverage factor and likewise the true body weight supported. But in all cases, the yieldable bending of the biasing means of this invention is that of a curvature or arcuate contour (e.g., a semi-circle) throughout substantially the entire length of the biasing means.

To be recognized also is that the length of biasing means in use affects the amount of "lift" by it. For example, a biasing member consisting of a bundle of 7 spring steel wires about 2.66 mm. in diameter tested to give "lift" of about 11 kilograms or about 25 pounds for a length of about 63 cm. or 25 inches; but the "lift" for this biasing member when at about 90 cm. or 30 inches was reduced by almost half. Thus the exact placement of holders when mounting biasing members can affect the lifting function thereof.

Further, as the thickness or diameter of individual wire elements is decreased, the "lifting" power per wire element decreases; but the ability of the wire to undergo greater and greater bending without taking on a permanent set increases. Thus, as the diameter of individual wire elements is decreased, a greater and greater number of such elements must be bundled in order to maintain a lift capacity equal to that for a biasing member of larger diameter units bundled together. This is because, as the cross sectional area of a wire is decreased, its flex strength or resistance to bending decreases much faster than linearly. For example, a ten percent decrease in the diameter of a wire can cause a decrease in flex strength or "lift" of about 30 percent or slightly more. Stated another way, for a decrease of about ten percent diameter, approximately 30 percent more wires of otherwise equal character are required to achieve approximately equal "lift". Even so, it is far more preferable to employ a bundle of resilient elements than to employ a single solid spring steel rod as a sole biasing member, both from the standpoint of avoidance of permanent set as well as the notably greater bendability with useful support.

A still further variable arises from the composition or alloy employed to form flexibly resilient members. Glass fibers or filaments as flexibly resilient biasing elements are relatively weak in terms of their resistance to bending and resilience of return to their original condition. A resilient member consisting of a resin bonded group of glass fibers also exhibits a relatively weaker "lift" or resistance to flexing as compared to an equal diameter or cross sectional size of spring steel wire, but a much greater degre of bend without taking on a permanent set.

Nevertheless, substantially straight flexibly resilient biasing members are advantageously formed by using aligned glass fibers as flexible elongated elements per se and embedding them in a flexible matrix of material, as aforenoted. The cross sectional size of round members of this type may be over a quarter centimeter in diameter up to slightly over a half centimeter in diameter, or slightly more, even a full centimeter or more. If the cross section employed is square or rectangular, a suitable size for a strong member may be a quarter centimeter or even a half centimeter in the bend direction up to a full cm. or so.* Despite the larger cross sectional size as compared to a biasing member exhibiting equal lift and consisting of a bundle of resilient metal wires, the glass fiber and resin composites are lighter in weight than an equivalent strength composite biasing member formed using metal wires. Additionally, the glass fiber and resin composites provide resulting biasing members which are highly resistant to taking on a permanent set on repeated bending during leg flexure.

*(A suitable thickness is 0.3 cm. to 0.6 cm. and a width of 0.5 cm. to 1.2 cm.) Thickness and width do not have to be the same for the entire length.

The force or weight required to initiate the bending of biasing means is less than the force or weight required to increase the bending at any later stage or degree of bending. Thus, the weight "lifted" or supported increases as the bending is increased beyond a 90° knee flexure or semi-circle for the biasing means; but a point is generally reached, on excessive bending, where danger of a permanent bend set arises. This increased resistance to bending as bending increases exhibits itself beneficially in a variety of ways, as for example, when a skier lands after jumping.

In light of all these variables, the terms "operable" or "effective" or "useful" or "significant" total lift or total support of a portion of body weight become appropriate as a practical and accurate manner of expressing the significant function performed by the biasing members to improve leg stamina. Even more appropriately, the portion of body weight supported is significant to reduce leg strain and improve stamina for repeated flexure.

The variables discussed above are equally applicable to strip or band members. In all cases the significant total lift or partial body support is in the range giving stamina improvement, and will generally be in the total lift range aforementioned. Noteworthy however is the fact that the width of strip biasing means may be relatively great without interference with leg function, even as great as 10 cm. or sometimes possibly 15 cm. wide. Greater widths allow for relative reduction of thickness while retaining comparable lift.

Users may sometimes desire to mount a device of this invention on their legs before putting on their pants or trousers. The holding means for the biasing means or members may comprise reinforced elements of a person's trousers or underwear or boots. That is, the biasing means or members may be built into apparel for the legs, with reinforced elements of the apparel functioning as the holding means for maintaining operable leg alignment. While noncoiled substantially straight biasing members have been found fully effective and reliable, and are greatly preferred, selective coiling, as for example, a single loop coil at the knee area, may give effective biasing strength and may possibly be employed if the coil bulk is not considered objectionable. The possibility also exists for the employment of members with some hinging rendered inoperable in use. Strap holders, especially for the knee or mid-portion of biasing members, may exhibit a slight or limited degree of elasticity, if desired.

That which is claimed is:

1. A leg aid device comprising elongated means for placement upon a user's leg and holding means for maintaining said elongated means upon the user's leg, wherein:

(a) said elongated means consists essentially of elongated flexibly resilient biasing means having a length sufficient for placement in approximate alignment with the user's leg from a level near the ankle area up to at least the level of the mid-thigh area and having a flexibility sufficient for said length to be repeatedly yieldingly bent into at least a semi-circle without taking on a permanent set, said biasing means, when held upon a body-supporting user's leg by the holding means hereinafter recited, functioning to support a portion of the user's body weight during times the user's leg is in flexed condition and functioning to aid the user's leg muscles in causing extension of the user's leg from a flexed condition, and (b) said holding means consists essentially of (i) a lower holder for fastening the lower end of said biasing means at a level near the user's ankle area, (ii) an upper holder for maintaining the upper end of said biasing means at a level at least as high as the user's mid-thigh area, and (iii) an intermediate holder comprising means for applying a forward pulling force transversely upon said biasing means at a mid-portion thereof at the level of the user's knee area, said intermediate holder being separate from said lower and upper holders but functioning in cooperation therewith to cause said biasing means to urge the user's leg toward a straightened condition without significant torsion or twisting of the user's leg and also functioning in cooperation therewith during leg flexure to cause said biasing means to take on an arcurate contour throughout substantially the entire length of said biasing means.

2. The device of claim 1 wherein said lower holder comprises means for allowing pivot movement of the lower end of said biasing means.

3. The device of claim 1 wherein said lower holder comprises holding means mounted on or part of the footwear of the user and wherein cooperative means at the lower end of said biasing means is provided for removably fastening said biasing means to said holding means.

4. The device of claim 1 wherein said upper holder consists essentially of means for solely contacting a rear portion of the user at a location at least as high as the user's mid-thigh area.

5. The device of claim 1 wherein said upper holder comprises a seat member.

6. The device of claim 1 wherein said biasing means comprises two elongated biasing members, each of which comprises a bundle of a plurality of elongated flexible elements, and wherein said intermediate holder comprises means for maintaining the mid-portion of said biasing members along opposite lateral portions of the user's knee level area.

7. The device of claim 6 wherein each said bundle comprises a flexible matrix of material within which said elongated flexible elements are embedded.

8. The device of claim 6 wherein said elongated flexible elements comprise flexible fibers and wherein each said bundle comprises a flexible matrix of material within which said fibers are embedded.

9. The device of claim 6 wherein said elongated flexible elements comprise resilient wires.

10. The device of claim 6 wherein said intermediate holder consists essentially of means for solely contacting a front portion of the user's leg.

11. The device of claim 6 wherein said intermediate holder comprises strap means for connecting said biasing members and extending solely over the front portion of the user's leg adjacent to the knee area thereof.

12. The device of claim 6 wherein said lower holder comprises structural means mounted on the footwear of a user and wherein cooperative means is provided at the lower end of said biasing members for removable fastening to said structural means.

13. A leg aid device for increasing the stamina of a body-supporting user's leg for repeated flexure and extension at the knee, comprising two elongated flexibly resilient biasing members for placement along opposite lateral portions of a user's leg in approximate alignment therewith from a level near the ankle area up to at least the level of the mid-thigh area, each said biasing member comprising a bundle of a plurality of elongated flexibly resilient biasing elements within a flexible sheath outer covering, said biasing members being adapted to bias a user's leg toward a straightened condition without significant torsion or twisting of the user's leg, and holding means for maintaining said biasing members approximately aligned upon a user's leg for bending yieldingly therewith during flexure thereof at the knee, said biasing members, when held by said holding means upon a body-supporting user's leg, functioning to support a portion of the user's body weight during times said biasing members are in bent condition with the user's leg in flexed condition, and functioning to aid the user's leg muscles in causing extension of the user's leg from flexed condition as said biasing members resiliently return toward a straightened condition with the extension of the user's leg.

14. A leg aid device for increasing the stamina of a body-supporting user's leg for repeated flexure and extension at the knee, comprising two elongated flexibly resilient biasing members for placement along opposite lateral portions of a user's leg in approximate alignment therewith from a level near the ankle area up to at least the level of the mid-thigh area, each said biasing member comprising a bundle of a plurality of elongated flexibly resilient biasing elements not embedded in any matrix for at least the major portion of their length and means uniting at least the upper ends of said biasing elements of a said bundle together in a manner obstructing longitudinal shift of one or more of said biasing elements with respect to the others thereof in said bundle, said biasing members being adapted to bias a user's leg toward a straightened condition without significant torsion or twisting of the user's leg, and holding means for maintaining said biasing members approximately aligned upon a user's leg for bending yieldingly therewith during flexure thereof at the knee, said biasing members when held by said holding means upon a body-supporting user's leg, functioning to support a portion of the user's body weight during times said biasing members are in bent condition with the user's leg in flexed condition, and functioning to aid the user's leg muscles in causing extension of the user's leg from flexed condition as said biasing members resiliently return toward a straightened condition with the extension of the user's leg.

15. A leg aid device for increasing the stamina of a body-supporting user's leg for repeated flexure and extension at the knee, comprising two elongated flexibly resilient biasing members for placement along opposite lateral portions of a user's leg in approximate alignment therewith from a level near the ankle area up to at least the level of the mid-thigh area, each said biasing member comprising a bundle of a plurality of elongated flexibly resilient biasing elements and a flexible matrix of material within which said elongated biasing elements are embedded along at least the major portion of their length, said biasing members being adapted to bias a user's leg toward a straightened condition without significant torsion or twisting of the user's leg, and holding means for maintaining said biasing members approximately aligned upon a user's leg for bending yieldingly therewith during flexure thereof at the knee, said biasing members, when held by said holding means upon a body-supporting user's leg, functioning to support a portion of the user's body weight during times said biasing members are in bent condition with the user's leg in flexed condition, and functioning to aid the user's leg muscles in causing extension of the user's leg from flexed condition as said biasing members resiliently return toward a straightened condition with the extension of the user's leg.

16. A leg aid device for increasing the stamina of a body-supporting user's leg for repeated flexure and extension at the knee, comprising two elongated flexibly resilient biasing members for placement in approximate alignment with a user's leg from a level near the ankle area up to at least the level of the mid-thigh area, said biasing members being adapted to bias a user's leg toward a straightened condition without significant torsion or twisting of the user's leg, and holding means for maintaining said biasing members approximately aligned upon a user's leg for bending yieldingly therewith during flexure thereof at the knee, said holding means including
(a) an upper holder for maintaining the upper portion of said members in spaced relationship at a level of a user's thigh area, said upper holder comprising a contoured seat member and means fastening said biasing members in spaced relationship to said seat member,
(b) a lower holder for maintaining the lower end of said members in spaced relationship at a level near a user's ankle area, and
(c) an intermediate holder for maintaining a mid-portion of said members along opposite lateral portions of a user's knee area,
said biasing members, when held by said holding means upon a body-supporting user's leg, functioning to support a portion of the user's body weight during times said biasing members are in bent condition with the user's leg in flexed condition, and functioning to aid the user's leg muscles in causing extension of the user's leg from flexed condition as said biasing members resiliently return toward a straightened condition with the extension of the user's leg.

17. A leg aid device for increasing the stamina of a body-supporting user's leg for repeated flexure and extension at the knee, comprising two elongated flexibly resilient biasing members for placement in approximate alignment with a user's leg from a level near the ankle area up to at least the level of the mid-thigh area, said biasing members being adapted to bias a user's leg toward a straightened condition without significant torsion or twisting of the user's leg, and holding means for maintaining said biasing members approximately aligned upon a user's leg for bending yieldingly therewith during flexure thereof at the knee, said holding means including
(a) an upper holder for maintaining the upper portion of said members in spaced relationship at a level of a user's thigh area,
(b) a lower holder for maintaining the lower end of said members in spaced relationship at a level near a user's ankle area, said lower holder comprising footwear having fastening means mounted thereon and cooperative means at the lower end of each said biasing member for removably fastening the same to said fastening means for pivotal movement of said biasing members with respect to said fastening means, and
(c) an intermediate holder for maintaining a mid-portion of said members along opposite lateral portions of a user's knee area,
said biasing members, when held by said holding means upon a body-supporting user's leg, functioning to support a portion of the user's body weight during times said biasing members are in bent condition with the user's leg in flexed condition, and functioning to aid the user's leg muscles in causing extension of the user's leg from flexed condition as said biasing members resiliently return toward a straightened condition with the extension of the user's leg.

18. A leg aid device for increasing the stamina of a body-supporting user's leg for repeated flexure and extension at the knee, comprising two elongated flexibly resilient biasing members for placement in approximate alignment with a user's leg from a level near the ankle area up to at least the level of the mid-thigh area, said biasing members being adapted to bias a user's leg toward a straightened condition without significant torsion or twisting of the user's leg, and holding means for maintaining said biasing members approximately aligned upon a user's leg for bending yieldingly therewith during flexure thereof at the knee, said holding means including
(a) an upper holder for maintaining upper portions of said members in spaced relationship at a level of a user's thigh area,
(b) a lower holder for maintaining the lower ends of said members in spaced relationship at a level near a user's ankle area, and
(c) an intermediate holder comprising knee cover means for maintaining a mid-portion of said members along opposite lateral portions of a user's knee area,
said biasing members, when held by said holding means upon a body-supporting user's leg, functioning to support a portion of the user's body weight during times said biasing members are in bent condition with the user's leg in flexed condition, and functioning to aid the user's leg muscles in causing extension of the user's leg from flexed condition as said biasing members resiliently return toward a straightened condition with the extension of the user's leg.

19. The device of claim 18 wherein said intermediate holder comprises a knee pad for fitting over the knee of a user and strap means for holding said biasing members along lateral portions of a user's knee area.

20. A leg aid device comprising elongated means for placement upon a user's leg and holding means for maintaining said elongated means upon the user's leg, wherein:
   (a) said elongated means consists essentially of elongated resilient biasing means comprising a strip member having a length sufficient for placement behind the leg of a user in approximate alignment with the user's leg from a level near the ankle area up to at least the level of the mid-thigh area and having a flexibility sufficient for said length to be repeatedly yieldingly bent into at least a semi-circle without taking on a permanent set, said biasing means, when held upon a body-supporting user's leg by the holding means hereinafter recited, functioning to support a portion of the user's body weight during times the user's leg is in flexed condition and functioning to aid the user's leg muscles in causing extension of the user's leg from a flexed condition, and
   (b) said holding means consists essentially of
      (i) a lower holder for fastening the lower end of said biasing means at a level near and behind the user's ankle area,
      (ii) an upper holder for maintaining the upper end of said biasing means at a level at least as high as and behind the user's mid-thigh area, and
      (iii) an intermediate holder comprising means for applying a forward pulling force transversely upon said biasing means at a mid-portion thereof at the level of and behind the user's knee area, said intermediate holder being separate from said lower and upper holders but functioning in cooperation therewith to cause said biasing means to urge the user's leg toward a straightened condition without significant torsion or twisting of the user's leg and also functioning in cooperation therewith during leg flexure to cause said biasing means to take on an arcuate contour throughout substantially the entire length of said biasing means.

21. The device of claim 20 wherein said strip member comprises a plurality of substantially aligned elongated flexible elements.

22. The device of claim 20 wherein said strip member comprises a flexible matrix and a plurality of substantially aligned flexible elements embedded in said matrix.

23. The device of claim 20 wherein said upper holder comprises receiving means for allowing longitudinal shift of the upper end of said strip member and fastening means for attaching said receiving means to a user.

24. The method of increasing the stamina of a leg for repeated flexure and extension at the knee in physical activity involving leg support of the body, said method comprising
   (a) forming elongated flexibly resilient biasing means having a length sufficient for placement in approximate alignment with said leg from a level near the ankle area up to at least the level of the mid-thigh area and having a flexibility sufficient for said length to be repeatedly yieldingly bent into at least a semi-circle without taking on a permanent set,
   (b) fastening the lower end of said biasing means at a level near the ankle area,
   (c) maintaining the upper end of said biasing means at a level at least as high as the mid-thigh area,
   (d) applying a forward pulling force transversely upon said biasing means at a mid-portion thereof at the level of the knee area, whereby said forward pulling force in combination with the fastened condition of the upper and lower ends of said biasing means causes said biasing means to urge said leg toward a straightened condition without significant torsion or twisting of said leg and causes said biasing means during leg flexure to take on an arcuate contour throughout substantially the entire length of said biasing means, and
   (e) repeatedly flexing and extending said leg at the knee, to thereby cause a portion of the weight of said body to be supported by said biasing means during times said leg is in flexed condition, and to thereby cause the muscles of said leg to be aided by said biasing means as said biasing means resiliently returns toward a straightened condition when said muscles extend said leg from a flexed condition.

25. The device of claim 1 wherein said upper holder comprises belt means adapted for wrapping about the user's hip area.

26. The device of claim 16 wherein said upper holder comprises belt means adapted for wrapping about the user's hip area.

27. The device of claim 20 wherein said upper holder comprises belt means adapted for wrapping about the user's hip area.

28. The method of claim 24 wherein said step of maintaining the upper end of said biasing means at a level at least as high as the mid-thigh area includes the act of fastening a belt about the hip area.

* * * * *